(12) United States Patent
Disilvestro et al.

(10) Patent No.: US 7,704,282 B2
(45) Date of Patent: *Apr. 27, 2010

(54) ORTHOPAEDIC ELEMENT WITH SELF-CONTAINED DATA STORAGE

(75) Inventors: Mark R. Disilvestro, Ft. Wayne, IN (US); Robert S. Hastings, Warsaw, IN (US); Terry L. Dietz, Columbia City, IN (US); Jason T. Sherman, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/887,947

(22) Filed: Jul. 9, 2004

(65) Prior Publication Data

US 2005/0010300 A1    Jan. 13, 2005

Related U.S. Application Data

(60) Provisional application No. 60/486,614, filed on Jul. 11, 2003.

(51) Int. Cl.
*A61F 2/30* (2006.01)
*A61B 5/07* (2006.01)

(52) U.S. Cl. .................. 623/18.11; 623/18.12; 600/587; 128/903

(58) Field of Classification Search ............... 623/18.11, 623/20.15, 20.14, 20.26, 20.27, 20.28, 20.29, 623/23.15, 23.16, 23.49, 22.4, 18.12, 20.32, 623/914; 600/300, 302, 587; 128/903; 606/73
See application file for complete search history.

(56) References Cited

U.S. PATENT DOCUMENTS 3,918,440 A * 11/1975 Kraus ........................ 602/2

| | | |
|---|---|---|
| 4,045,825 A | 9/1977 | Stroot |
| 4,675,670 A | 6/1987 | Lalonde et al. |
| 5,047,054 A * | 9/1991 | Vijayan et al. ............. 623/23.6 |
| 5,197,488 A * | 3/1993 | Kovacevic .................. 600/595 |
| 5,292,252 A * | 3/1994 | Nickerson et al. ........... 433/173 |
| 5,300,120 A | 4/1994 | Knapp et al. |
| 5,376,128 A | 12/1994 | Bozeman |
| 5,383,915 A | 1/1995 | Adams |

(Continued)

FOREIGN PATENT DOCUMENTS

WO    WO 00/65981    11/2000

(Continued)

OTHER PUBLICATIONS

Bhadra, Niloy, M.D., et al; Implementation of an Implantable Joint-Angle Transducer (2002). J. Rehab Res Dev, 39(3).

(Continued)

*Primary Examiner*—Pedro Philogene (57) ABSTRACT

An orthopaedic element has an information storage portion. A transmitter portion and an internal power source portion may be associated with the body of the orthopaedic element. Information, such as data related to the orthopaedic element, patient or caregiver can be stored in the information storage portion. The transmitter portion is coupled to the information storage portion and the internal power source portion. The stored information is selectively transmitted to an external receiver and data interpretation device.

5 Claims, 6 Drawing Sheets

U.S. PATENT DOCUMENTS

| | | | |
|---|---|---|---|
| 5,395,033 A | 3/1995 | Byrne et al. | |
| 5,458,655 A | 10/1995 | Bozeman | |
| 5,465,619 A | 11/1995 | Sotack et al. | |
| 5,480,454 A | 1/1996 | Bozeman | |
| 5,769,875 A | 6/1998 | Peckham et al. | |
| 5,776,171 A | 7/1998 | Peckham et al. | |
| 5,831,430 A | 11/1998 | Pfanstiehl et al. | |
| 5,954,758 A | 9/1999 | Peckham et al. | |
| 6,026,328 A | 2/2000 | Peckham et al. | |
| 6,034,296 A * | 3/2000 | Elvin et al. | 623/16.11 |
| 6,120,540 A * | 9/2000 | Apple et al. | 623/11.11 |
| 6,163,725 A | 12/2000 | Peckham et al. | |
| 6,228,900 B1 | 5/2001 | Shen et al. | |
| 6,239,705 B1 | 5/2001 | Glen | |
| 6,245,109 B1 * | 6/2001 | Mendes et al. | 623/18.11 |
| 6,281,264 B1 | 8/2001 | Salovey et al. | |
| 6,281,679 B1 | 8/2001 | King et al. | |
| 6,332,089 B1 | 12/2001 | Acker et al. | |
| 6,400,272 B1 | 6/2002 | Holtzman et al. | |
| 6,400,989 B1 | 6/2002 | Eckmiller | |
| 6,402,689 B1 | 6/2002 | Scarantino et al. | |
| 6,447,448 B1 | 9/2002 | Ishikawa et al. | |
| 6,454,781 B1 | 9/2002 | Witt et al. | |
| 6,473,652 B1 | 10/2002 | Sarwa et al. | |
| 6,498,944 B1 | 12/2002 | Ben-Haim et al. | |
| 6,503,249 B1 * | 1/2003 | Krause | 606/62 |
| 6,507,189 B2 | 1/2003 | Woolsey et al. | |
| 6,558,229 B2 | 5/2003 | Kimura et al. | |
| 6,563,308 B2 | 5/2003 | Nagano et al. | |
| 6,573,706 B2 | 6/2003 | Mendes et al. | |
| 6,583,630 B2 | 6/2003 | Mendes et al. | |
| 6,599,321 B2 * | 7/2003 | Hyde, Jr. | 623/18.12 |
| 6,610,096 B2 * | 8/2003 | MacDonald | 623/18.11 |
| 6,679,920 B2 | 1/2004 | Biedermann et al. | |
| 6,687,131 B1 | 2/2004 | Miehling | |
| 6,706,005 B2 * | 3/2004 | Roy et al. | 600/594 |
| 6,947,004 B2 | 9/2005 | Mejia et al. | |
| 2001/0000187 A1 | 4/2001 | Peckham et al. | |
| 2002/0133175 A1 | 9/2002 | Carson | |
| 2002/0147455 A1 | 10/2002 | Carson | |
| 2004/0008123 A1 * | 1/2004 | Carrender et al. | 340/825.49 |
| 2004/0034355 A1 | 2/2004 | Govari et al. | |

FOREIGN PATENT DOCUMENTS

| | | | |
|---|---|---|---|
| WO | WO 03/090974 | * | 11/2003 |

OTHER PUBLICATIONS

Bragdon, C.R., et al; Experimental assessment of precision and accuracy of radiostereometric analysis for the determination of polyethylene wear in a total hip replacement model. Journal of Orthopaedic Research, 2002, pp. 688-695, 20.

Cicuttini, F. M., et al; Tibial and femoral cartilage changes in knee osteoarthritis. Ann Rheum Dis Oct. 2001; pp. 977-980, 60.

Conrozier, T., et al; Quantitative radiography in osteoarthritis: Computerized measurement of radiographic knee and hip joint space. Bailliere's Clinical Rheumatology, Aug. 1996, pp. 429-433, vol. 10, No. 3.

Graichen, F., et al; Four-Channel Telemetry System for In Vivo Measurement of Hip Joint Forces (1991). J. Biomed. Eng. 1991, vol. 13, September.

Graichen, F., et al; Inductively Powered Telemetry System for In Vivo Measurement With Orthopaedic Implants (1995); Biotelemetry XIII, Mar. 26-31, 1995—Williamsburg, VA.

Hilliquin, P., et al; Quantitative assessment of joint space width with an electronic caliper; Osteoarthritis and Cartilage Jul. 2002; pp. 542-546, 10.

Hyldahl, H.C.,MD, et al; Does Metal Backing Improve Fixation of Tibial Component in Unicondylar Knee Arthroplasty? A Randomized Radiostereometric Analysis. The Journal of Arthroplasty, 2001, pp. 174-179, vol. 16 No. 2.

Ilchmann, T., Thesis Radiographic assessment of cup migration and wear after hip replacement. Acta Orthopaedica Scandinavica, Oct. 1997, vol. 68, No. 276.

Johnson, Mark W., et al; Implantable Transducer for Two-Degree of Freedom Joint Angle Sensing (1999). IEEE Trans Rehab Eng, pp. 349-359 7(3).

Karrholm, J., MD, et al; Radiostereometry of Hip Prostheses Review of Methodology and Clinical Results, Clinical Orthopaedics and Related Research, 1997, pp. 94-110 No. 344.

Lanyon, P., et al; Radiographic assessment of symptomatic knee osteoarthritis in the community: definitions and normal joint space. Ann Rheum Dis 1998, pp. 595-601 No. 57.

Miller, Joel S., et al; Molecule-Based Magnets—An Overview (2000). MRS Bulletin, November.

Onsten I, et al; Wear in uncemented porous and cemented polyethylene sockets: A Randomised, Radiosterometric Study. The Journal of Bone and Joint Surgery Br, Mar. 1998; pp. 345-350, 80(2).

Pavelka, K., et al; Correlation between knee roentgenogram changes and clinical symptoms in osteoarthritis. Rev. Rhum. Mal. Osteoartic., 1992, pp. 553-559, 59 (9).

Ryd, L., et al; Methods for determining the accuracy of radiostereometric analysis (RSA), Acta Orthopaedic Scandinavica, 2000, pp. 403-408, 71 (4).

Seedhom, B.B., et al; A Technique for the Study of Geometry and Contact in Normal and Artificial Knee Joints (1972). Wear—Elsevier Sequoia S.A., Lausanne—Printed in the Netherlands.

Selvik, G., Roentgen stereophotogrammetry A method for the study of the kinematics of the skeletal system. Acta Orthopaedica Scandinavica, 1989, vol. 60, No. 232, Munksgaard Copenhagen.

Sychterz, Christi J., MS, et al; Effect of Radiographic Quality on Computer-Assisted Head Penetration Measurements. Clinical Orthopaedics and Related Research, 2001, pp. 150-158, No. 386.

Troyk, Philip R., et al; Design and Implementation of an Implantable Goniometer (1986); IEEE Transactions on Biomedical Engineering, vol. BME-33, No. 2, February.

Vrooman, H,A., et al; Fast and accurate automated measurements in digitized stereophotogrammetric radiographs. Journal of Biomechanics, 1998, pp. 491-498, 31.

Want, Roy, "RFID-A Key to Automating Everything", Jan. 2004, (13 pages).

* cited by examiner

ORTHOPAEDIC ELEMENT WITH SELF-CONTAINED DATA STORAGE

CROSS-REFERENCE TO RELATED APPLICATIONS

This application claims priority to U.S. Provisional Application Ser. No. 60/486,614 filed on Jul. 11, 2003 by Mark R. DiSilvestro, entitled "In Orthopaedic Element With Self-Contained Data Storage," which is incorporated by reference herein in its entirety.

FIELD OF THE INVENTION

The present invention relates to orthopaedic elements and the need for accessible information regarding the orthopaedic elements. More particularly, the present invention relates to the provision of orthopaedic elements with specific information provided with the orthopaedic elements. The specific information may encompass data regarding the patient, the source of the orthopaedic element, and the caregiver.

BACKGROUND OF THE INVENTION

Human bones can become damaged as a result of accident or illness. Such damage can be, for example, to the articular cartilage covering the ends of the bones at a joint as well as the intra-articular cartilage between the ends of the adjacent bones of the joint. When the damage to the joint is severe, a joint endoprosthesis can be implanted to improve the comfort and mobility of the patient.

Joint endoprostheses have been developed to replace native tissue of several human joints. There are a variety of knee prostheses, hip prostheses, shoulder prostheses, ankle prostheses and wrist prostheses available to relieve patient suffering. Such devices are made by and available from, for example, DePuy Products, Inc. and DePuy Orthopaedics, Inc. of Warsaw, Ind.

Standard joint endoprostheses include metal components that are affixed to the articulating ends of the bones of the joint and commonly include a bearing component positioned between the metal components. Standard bearing components of joint endoprostheses have a surface against which one of the metal components articulates. For example, hip endoprostheses include a metal femoral component to be affixed to the proximal femur and a metal cup to be affixed to the acetabulum. Many of these standard hip endoprostheses include a liner in the acetabular cup against which the femoral component articulates. Knee prostheses commonly include a femoral component to be affixed to the distal femur and a tibial component to be affixed to the proximal tibia. Bearings are typically between the femoral and tibial components. Similar systems with bearings are available to replace other joints in the body. Such endoprosthesis systems are commercially available from DePuy Orthopaedics, Inc. of Warsaw, Ind.

Orthopaedic prosthetics are also used to replace bone lost in the treatment of various bone cancers. These orthopaedic prosthetics may include elements of a joint endoprosthesis as well as components to replace intercalary bone loss. Such prosthetics are made by and available from DePuy Products, Inc. and DePuy Orthopaedics, Inc. of Warsaw, Ind.

Trauma products are also available for treating patients suffering traumatic injury, such as bone fractures. Trauma products frequently include orthopaedic components such as bone screws, bone nails, bone plates and fixators, for example. Such trauma products are commercially available from DePuy Trauma and Extremities of Warsaw, Ind.

A wide variety of orthopaedic instrument sets are also available for use is implanting such orthopaedic prosthetics and trauma products. Such instrument sets commonly include a plurality of individual instruments. DePuy Orthopaedics, Inc. supplies such instrument sets to orthopaedic surgeons.

For a variety of orthopaedic implants, a surgical kit also includes a plurality of orthopaedic trial components that the orthopaedic surgeon temporarily attaches to the bone before permanently affixing the orthopaedic implants. DePuy Orthopaedics, Inc. supplies such trials with its surgical kits for implantation of joint endoprostheses.

SUMMARY OF THE INVENTION

The present invention addresses the need to provide readily accessible data for identifying and retrieving data from orthopaedic elements.

In one aspect, the present invention provides an orthopaedic element comprising a body, an information storage portion associated with the body, a transmitter portion associated with the body, and an internal power source portion associated with the body. The transmitter is coupled to the information storage portion for transmitting a signal related to the information stored in the information storage portion. The internal power source portion is associated with the body and connected to supply power to the transmitter.

In another aspect, the present invention provides an orthopaedic element that includes a component for storing information and selectively transmitting the stored information.

In another aspect, the present invention provides a joint endoprosthesis comprising a first prosthetic component to be affixed to one bone of the joint and a second prosthetic component to be affixed to another bone of the joint. At least one of the first and second prosthetic components includes an information storage portion, a transmitter portion and an internal power source portion. The transmitter portion is provided for transmitting a radio-frequency signal that has a characteristic related to the information stored in the information storage portion. The internal power source portion is provided for selectively supplying power to the transmitter portion.

In another aspect, the present invention provides a joint endoprosthesis comprising a first prosthetic component to be affixed to one bone of the joint and a second prosthetic component to be affixed to another bone of the joint. The first prosthetic component includes a body, an information storage portion, a transmitter portion and an internal power source portion. The information storage portion, transmitter portion and internal power source portion are associated with the body. The transmitter portion serves to transmit a radio-frequency signal that has a characteristic that is related to the information stored in the information storage portion. The internal power source portion is connected to selectively supply power to the transmitter portion. The second prosthetic component also includes a body, an information storage portion, a transmitter portion and an internal power source portion. The information storage portion, transmitter portion and internal power source portion are associated with the body. The transmitter portion serves to transmit a radio-frequency signal that has a characteristic that is related to the information stored in the information storage portion. The internal power source portion is connected to selectively supply power to the transmitter portion.

In another aspect, the present invention provides a method of retrieving information related to an orthopaedic element.

The method comprises the steps of storing information related to the orthopaedic element on the orthopaedic element and transmitting a signal related to the stored information. The signal is transmitted from the orthopaedic element.

In another aspect, the present invention provides an orthopaedic element comprising a body including an assembly of a carrier element and at least one of the following: an orthopaedic prosthetic component, an orthopaedic trauma product, an orthopaedic instrument, and an orthopaedic trial. The orthopaedic element further comprises an information storage portion associated with the carrier element.

BRIEF DESCRIPTION OF THE DRAWINGS

The invention will be better understood by reference to the figures of the drawings wherein like numbers denote like parts throughout and wherein.

DETAILED DESCRIPTION OF THE ILLUSTRATED EMBODIMENTS

The teachings of the present invention are broadly applicable to all orthopaedic elements. As used herein, "orthopaedic element" is intended to broadly include orthopaedic prosthetic components, trauma products, orthopaedic instruments and orthopaedic trials. "Orthopaedic prosthetic components" is intended to broadly include joint endoprostheses as well as intercalary prosthetics. "Joint endoprostheses" is intended to include knee, hip, shoulder, wrist, and ankle endoprostheses and endoprostheses for use with the digits of the extremities. "Trauma products" is intended to include products used in treating orthopaedic trauma, including bone nails, bone screws, fixator systems, and bone plates. "Orthopaedic instruments" is intended to include surgical instruments intended for use during the implantation of orthopaedic prosthetic components and trauma products. "Orthopaedic trials" is intended to include trials for use in the implantation of orthopaedic prosthetic components.

Figure 1:
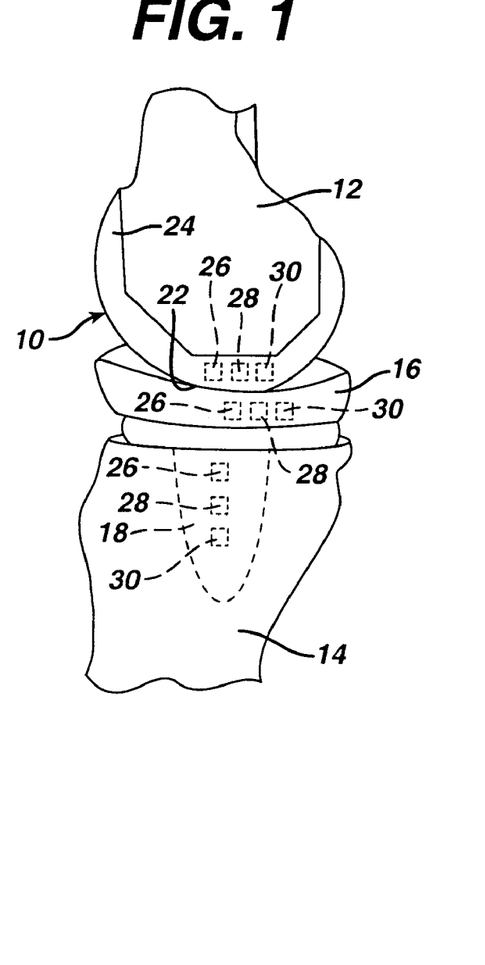
FIG. 1 is a side elevation of a knee joint endoprosthesis implanted on a distal femur and proximal tibia.
Figure 2:
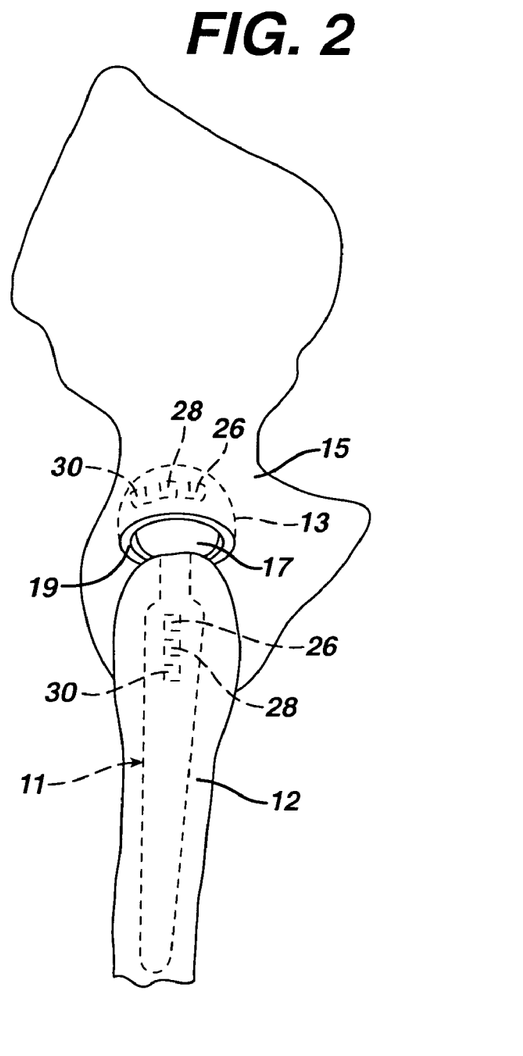
FIG. 2 is a side elevation of a hip joint endoprosthesis system implanted on a portion of the hipbone and proximal femur.
Figure 3:
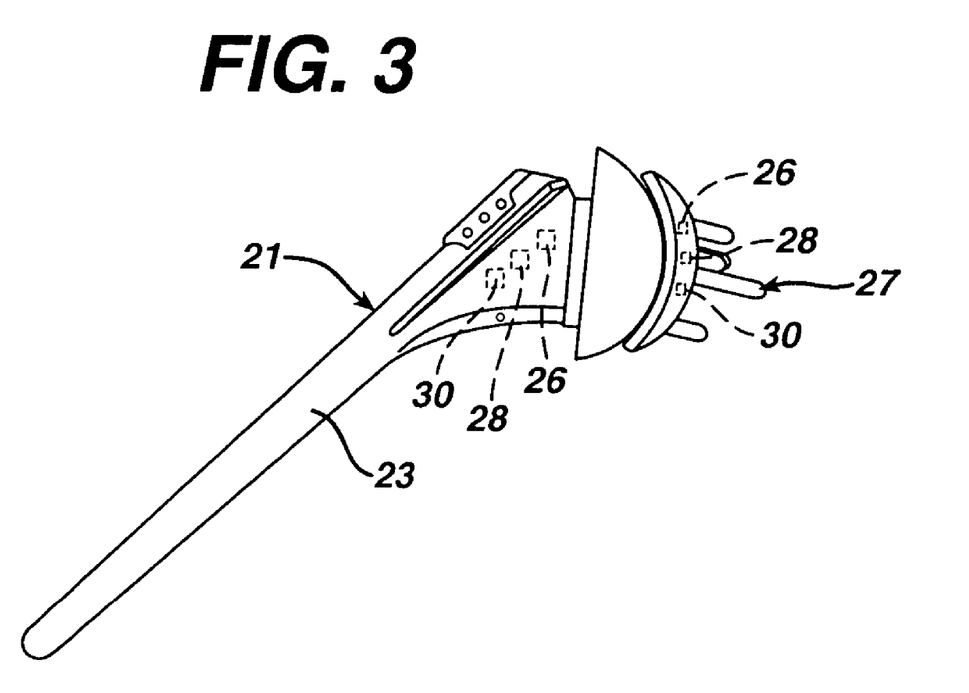
FIG. 3 is a side elevation of a shoulder joint prosthesis system.
Figure 8:
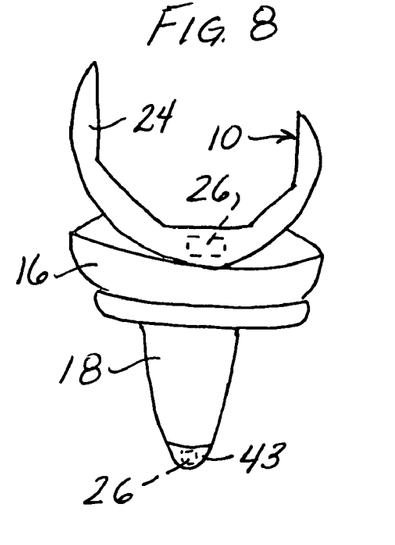
FIG. 8 is a side elevation of a knee joint endoprosthesis.
Figure 9:
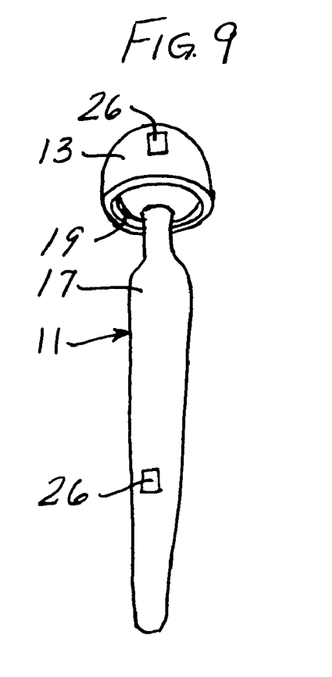
FIG. 9 is a side elevation of a hip joint endoprosthesis system.
Figure 10:
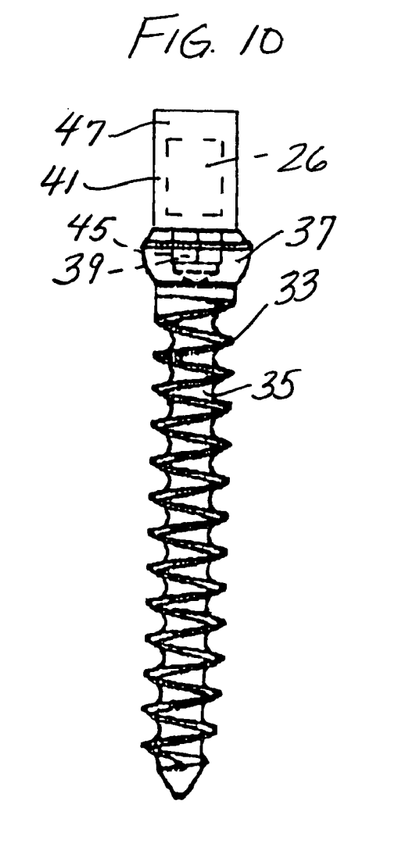
FIG. 10 is an elevation of an assembly of a bone screw and a carrier element.

FIGS. 1 and 8 illustrate knee joint endoprostheses. FIGS. 2 and 9 illustrate hip joint endoprostheses. FIG. 3 illustrates a shoulder joint endoprosthesis. FIG. 10 illustrates a trauma product, more specifically, a bone screw.

Referring first to FIG. 1, a knee endoprosthesis 10 incorporating the principles of the present invention is illustrated implanted on the distal end of the femur 12 and proximal end of the tibia 14. The illustrated knee endoprosthesis 10 includes a tibial bearing 16 that is carried by the proximal tibial component 18. The proximal tibial component 18 is affixed to the proximal end of the tibia 14. The tibial bearing 16 has a contoured proximal surface, against which the condyles 22 of the distal femoral component 24 bear. The distal femoral component 24 is affixed to the distal end of the femur 12. Articulation of the joint is at the interface of the proximal surface of the tibial bearing 16 and the condyles 22 of the distal femoral component 24.

In FIG. 2, the hip endoprosthesis 11 is illustrated with an acetabular cup or shell 13 implanted on the patient's hip bone 15 and with a proximal femoral component 17 implanted on the patient's femur 12. The illustrated hip endoprosthesis 11 also includes an acetabular liner 19 interposed between the acetabular cup 13 and the femoral component 17.

In FIGS. 8 and 9, like reference numerals have been used for like parts of the endoprostheses. In the embodiment of FIG. 8, the tibial component 18 comprises an assembly of an integral tibial tray and stem with an end plug 43.

In FIG. 3, a shoulder endoprosthesis 21 is illustrated. The illustrated shoulder endoprosthesis comprises a humeral component 23 and a glenoid component 27.

In FIG. 10, the bone screw 33 includes a threaded screw body 35 and a head 37 with a hexagonal opening 39 to receive a portion of a surgical instrument (not shown) for driving the screw into the patient's bone. The embodiment of FIG. 10 comprises an assembly of the bone screw 33 and a detachable carrier element 41.

In the illustrated embodiments, the proximal tibial component 18, distal femoral component 24, proximal femoral component 17, acetabular cup or shell 13, humeral component 23 and bone screw 33 are made of standard materials such as metal such as cobalt-chrome or titanium. The tibial bearing 16, acetabular liner 19 and glenoid component 27 are made of standard materials such as polyethylene. Other standard materials such as metal and ceramic can be used for the bearings. These materials are provided as examples only, and the present invention is not limited to any particular material unless expressly called for in the claims.

In the embodiments of FIGS. 1-3 and 8-9, each of the orthopaedic prosthetic components 13, 16, 17, 18, 19, 21, 23, 24 and 27 comprises a body. An information storage portion 26 is associated with the body of each of the prosthetic components 13, 16, 17, 18, 21, 23, 24 and 27.

Figure 11:
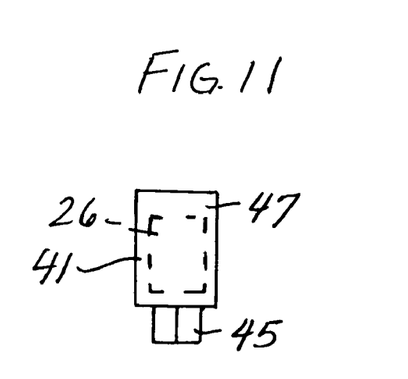
FIG. 11 is an elevation of the carrier element of the FIG. 10 assembly.

In the embodiment of FIG. 10, the assembly of the bone screw 33 and the carrier element 41 comprises a body; an information storage portion 26 is carried by the carrier element 41 and is thereby associated with the body. Although not shown in FIG. 2, an information storage portion 26 could also be associated with the acetabular liner 19. As shown in FIG. 11, the carrier portion 41 of the bone screw 33 includes a male portion 45 and a body portion 47. The male portion 45 is hexagonally shaped to mate with the hexagonal opening 39 in the head 37 of the bone screw. The fit of the mating male portion 45 and opening 39 is tight enough so that the carrier element 41 does not come loose from the screw unless the two components are pulled apart. The body portion 47 of the carrier element 41 may be of any desired shape; in the illustrated embodiment, the body portion 47 is cylindrical in shape. It should be understood that the mating shapes of the male portion 45 and opening 39 illustrate one example of a mechanical connection between these components; other types of mechanical connection can be used, such as a press fit, taper fit, snap fit or threaded connection for example. The carrier element 43 of the FIG. 8 embodiment is connected to the distal end of the tibial stem through a threaded screw connection. In use, the surgeon or other caregiver can remove the carrier element 41 intraoperatively, after using its information to confirm that the bone screw is of the desired size and type; the carrier element 43 can be left connected to the tibial stem and implanted with the tibial component if desired. It should also be understood that the information storage portion 26 could include other types of data recordation, such as a bar code for example. It should also be understood that similar carrier elements 41, 43 can be used with other orthopaedic elements as well as those illustrated.

As illustrated in the embodiments of FIGS. 1-3 and 8-10, the information storage portion 26 can be associated with the body in different ways. In the embodiments of FIGS. 1-3 and in the femoral component of FIG. 8, the information storage portion 26 is held permanently within a recess in the component itself. In the embodiment of FIG. 9, the two information storage portions 26 are affixed to the exterior of the orthopaedic prosthetic components through the use of a suitable biocompatible adhesive. It should be understood that the information storage portions 26 of FIG. 9 could alternatively be mechanically fixed to the exterior surfaces of the orthopaedic prosthetic components. In the case of the tibial component of the embodiment of FIG. 8, the information storage portion 26 is carried within the end plug 43; the end plug 43 is mechanically connected to the distal end of the tibial stem in a standard manner. In the case of the bone screw of FIG. 10, the information storage portion 26 is part of the detachable carrier 41. It should be understood that the foregoing are provided as different examples of the manner in which the information storage portion 26 can be associated with the body of the orthopaedic elements.

The information storage portion 26 of the orthopaedic element may be an electronic chip capable of recording information or data for later retrieval. Suitable information storage elements 26 are available from Texas Instruments of Dallas, Tex. and from SOKYMAT Identification USA, Inc. of Cynthiana, Ky. (www.sokymat.com). The information stored on the information storage portion 26 can include, for example, specific information about the implant itself, such as manufacturer information, material information, part number, catalog number, lot number and other information that might be useful in identifying the prosthetic component. Alternatively, the information stored could be a unique identifier. Storage of such information would be beneficial in the manufacture, packaging, storage and distribution of such orthopaedic elements. For example, it would be helpful to have access to such product-identifying information after the orthopaedic element has been packaged. Access to such information could be helpful in inventory control and product distribution for example. For such uses, the information storage portion 26 can be a "read-only" one that cannot record additional information after leaving the manufacturer's hands. The information stored on the information storage portion 26 could also include other data. For example, a read/write information storage portion 26 could allow the caregiver to record additional information on the information storage element at the point of care. For example, patient medical or surgical records could be written onto the information storage portion 26 at the time of surgery and be available for retrieval at a later time and place. The ready availability of this information would be valuable, for example, for emergency room treatment of a patient if external medical and surgical records are not readily available. In addition, with various security systems utilizing metal detection equipment, it may be desirable to provide security personnel with a quick and easy method of determining that a positive metal scan results from the presence of an implant.

Although the information storage portion 26 may serve to store information electronically, it should be understood that other types of data storage may be used. For example, information could be stored magnetically or through use of radio-opaque labeling.

Magnetic storage of information in the information storage portion 26 can be accomplished through use of materials such as paramagnets and superparamagnets, for example. Paramagnets and superparamagnets typically contain ferrite or a similar iron oxide compound encased or distributed in a polymer. In the case of superparamagnets, the metal compound is usually provided in the form of very small magnetic particles, such as microspheres (below about 100-150 nm) which, because their size is under a critical value, do not behave any longer as small autonomous magnets, that is, they will align in a preferential direction only when subjected to an external magnetic field. Use of a superparamagnetic material as the information storage portion 26 is anticipated to be useful in that the material should be compatible with magnetic resonance imaging and does not retain magnetization unless subjected to selected conditions. In the present invention, the magnetic particles can be distributed in a suitable biocompatible polymer, and could be arranged in the form of a two or three-dimensional barcode or other unique dispersion or array. To use such paramagnetic and superparamagnetic materials, the caregiver would be provided with an external field source not shown that serves to selectively magnetize the information storage portion. The caregiver would also be provided with an appropriate sensor to sense some characteristic of the magnetic field; examples of such magnetic sensors include: Hall effect sensors (including three-dimensional Hall effect sensors); variable reluctance sensors; magnetoelastic sensors; magnetoresistive sensors; magnetorestrictive sensors; saturation core (flux-gate) sensors; superconducting quantum interference devices (SQUIDS); nuclear magnetic resonance sensors; induction core magnetometers; proton precession magnetometers; and optically pumped magnetometers. All of these sensors are capable of sensing at least one property of the magnetic field of the paramagnets or superparamagnets, the properties including electromagnetic and magnetostatic fields.

To allow for easy access to the data stored on each information storage portion 26, each of the illustrated prosthetic components 13, 16, 17, 18, 19, 21, 23, 24 and 27 of the embodiments of FIGS. 1-3 also may include electronic portions 28 and an internal power source portion 30 for selectively transmitting the stored information.

Figure 4:
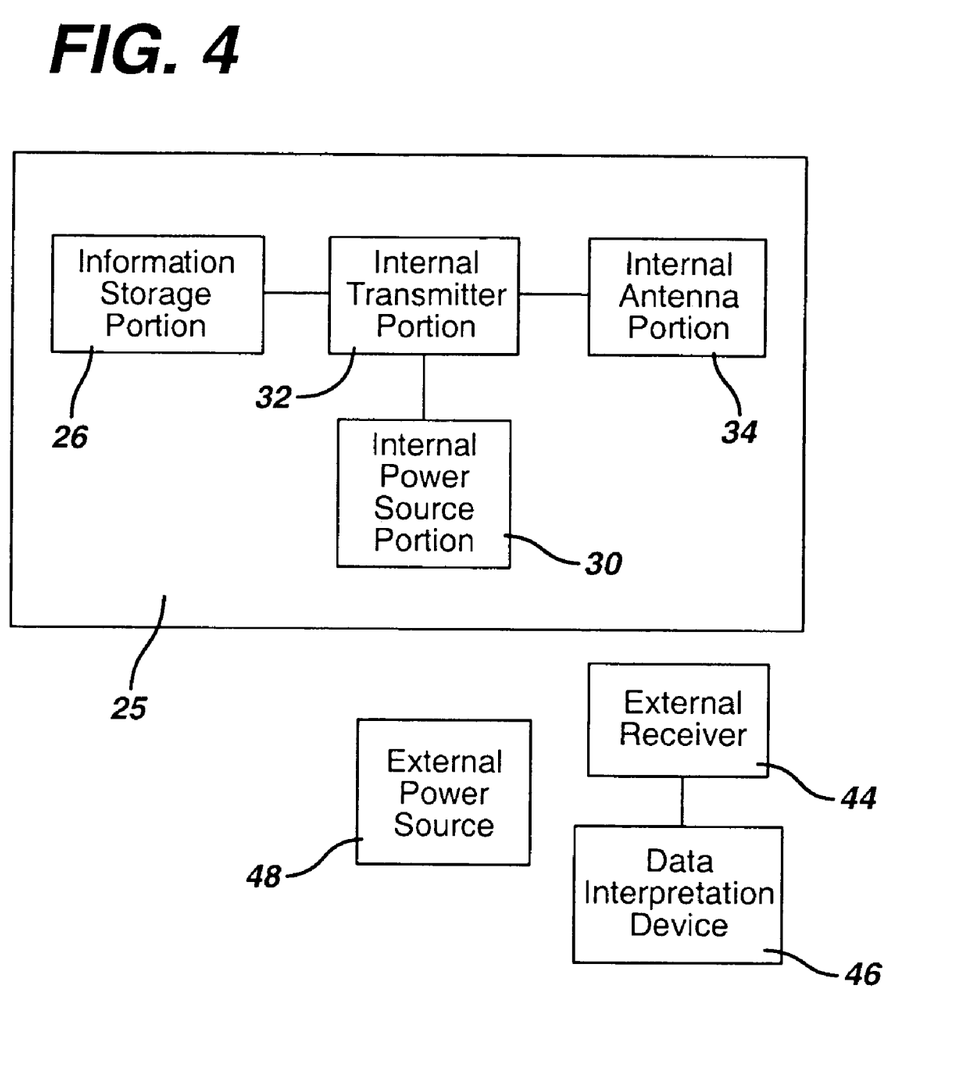
FIG. 4 is a schematic illustration of an orthopaedic element, showing external components as well as those associated with the orthopaedic element.

As shown schematically in FIG. 4, the electronic portions 28 of the embodiments of FIGS. 1-3 comprise a transmitter 32 and an internal antenna portion 34. The transmitter 32 is electrically connected or coupled to the information storage portion 26, to the internal power source portion 30 and to the internal antenna portion 34. In FIG. 4, the body of the orthopaedic element is indicated generally at 25. It should be understood that the body 25 could comprise the body of the femoral component 24, the body of the tibial bearing 16, or the body of the tibial component 18 of the FIG. 1 embodiment; the body 25 could comprise the body of the acetabular shell 13, the femoral component 17 or the acetabular liner 19 in the FIG. 2 embodiment; and the body 25 could comprise the humeral component 23 or the glenoid component 27 of the shoulder endoprosthesis 21 illustrated in FIG. 3. The body 25 could also comprise the analogous parts of other prosthetic systems. The body 25 illustrated in FIG. 4 could also comprise: a portion of a surgical instrument; a trauma product such as a bone screw; a trial such as a femoral, tibial, or acetabular trial; or an intercalary prosthetic for example. As discussed herein the body can also comprise an assembly of any of the above elements and a carrier element.

The transmitter 32 may comprise a radio-frequency transmitter for example. Suitable internal radio-frequency transmitters 32 are commercially available from Texas Instruments Inc. in the form of electronic chips. The desired characteristics of the transmitter 32 may vary depending on other components of the system; in general, the transmitter will be of an appropriate size for implantation, will transmit at a desired frequency and will not consume excessive power. However, it should be understood that the present invention is not limited to any particular type of transmitter or transmission signal unless expressly called for in the claims.

Other possible types of transmitters and types of signals include optical data transmission. An IBM personal area network may also be usable as a transmitter. Acoustic energy transmission, capacitive telemetry (using electric fields) and inductive telemetry (using magnetic fields) are also possible alternatives for transmission in the present invention.

The internal antenna portion 34 may be hermetically sealed. A suitable internal antenna portion 34 is available from Texas Instruments, Inc and Sokymat. However, it should be understood that the present invention is not limited to use of an internal antenna or to any particular type of internal antenna unless expressly called for in the claims.

Both the internal transmitter portion 32 and/or the internal antenna portion 34 should be capable of transmitting a signal to the exterior of the patient's body. Accordingly, the internal transmitter portion 32 and/or the internal antenna portion 34 should be capable of transmitting a signal through the metal or other material forming the body or the carrier element of the orthopaedic element with which they are associated.

The internal transmitter portion 32 is electrically connected to the internal antenna portion 34, and is electrically connected to be powered by the internal power source portion 30. The internal power source portion 30 could be an active power source or a passive power source. For an active power source, a battery could be used for the internal power source 30. A passive power supply or source may be desirable to use to conserve power; with a passive power source, the electronic portions will be powered when external power excitation is present, such as through inductive coupling to an internal coil. Such a passive power source will selectively supply power to the transmitter 32 and if necessary to the internal antenna 34.

The internal power source portion 30 may be a passive power source comprising an inductive power source such as ferrite coil. A suitable ferrite coil is a small wound coil available commercially from MicroStrain, Inc. of Williston, Vt. The necessary characteristics of such a wound coil will depend to some extent on the design and selection of the other electronic components; power, frequency and size of the coil can be adjusted to suit the other components of the system. Alternatively, a suitable ferrite coil could be wound using standard equipment such as that available from Aumann North America, Inc. of Fort Wayne, Ind. It should be understood that the use of a ferrite coil is provided as an example of an internal power source; the present invention is not limited to the use of a ferrite coil unless expressly called for in the claims.

Another alternative for selectively supplying power to the transmitter portion is to use an internal battery with an inductively activated switch to selectively draw power from the battery. Other alternative power sources are available.

In the case of orthopaedic elements utilizing radio-opaque material or magnetic material for data storage, a transmitter, internal power source and antenna would not be needed.

Figure 5:
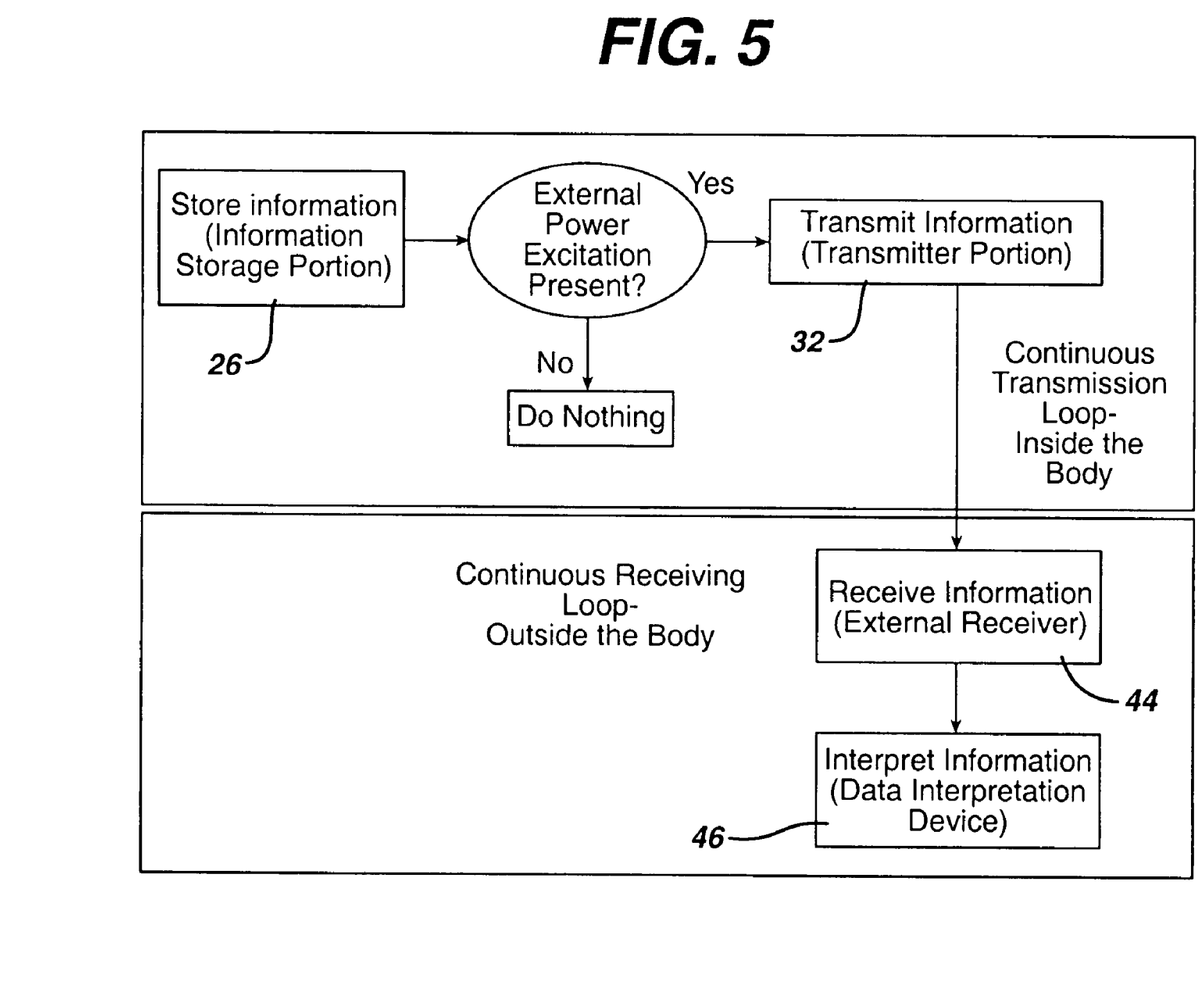
FIG. 5 is a flow chart illustrating use of the orthopaedic element of FIG. 3.

As shown schematically in FIGS. 4-5, an external receiver 44 and data interpretation device 46 can be provided at a manufacturing or distribution site, at a security screening station, or at the point of care, such as in a physician's office or at a hospital. For the embodiments utilizing a radio-frequency transmitter, the external receiver 44 can comprise a radio-frequency antenna that is connected to receive the signature signal from the internal antenna 34 and to provide a signature signal to the data interpretation device 46. It will be appreciated that other types of external receivers would be used for signals other than radio-frequency signals. For example, the magnetic sensors described above can be used in embodiments utilizing magnetic data storage. In the case of radio-opaque markers on radiolucent materials (such as on radiolucent carriers) as the storage portion, the external receiver can comprise a standard radiography equipment.

The external receiver 44 can include circuitry to demodulate the signal and to generate a suitable input for the data interpretation device 46. Typically, in the case of devices utilizing radio-frequency signals, the external receiver 44 typically amplifies, filters, demodulates and digitizes the signals. The data interpretation device 46 can be a standard computer programmed to interpret the radio-frequency transmittal signal or a digitized signal received from the internal transmitter 32, internal antenna 34 and external receiver 44.

If the internal power source portion 30 comprises an inductor, an external power source 48 can also be provided at the manufacturing location, screening site or point of care. The external power source 48 can comprise an external coil that generates a strong localized magnetic field that is inductively coupled to the implanted ferrite coil (internal power source) to thereby supply power to the implanted electronics. Suitable external coils are commercially available from Microstrain Inc. of Williston, Vt. Alternatively, a suitable ferrite coil could be wound using standard equipment such as that available from Aumann North America, Inc. of Fort Wayne, Ind. Generally, since the external coils are likely to be used in close proximity to the patient, it may be desirable to select or design an external coil that will not irritate or excessively heat the patient's skin and that can be easily handled by the operator or medical technician. The external coil should be able to supply a sufficient electromagnetic field at the design frequency to stimulate the internal power coil.

FIG. 5 illustrates a possible flow diagram for information for the first illustrated embodiment of the present invention. If there is no external power source, the implanted electronics remain inactive. When an external power source is applied, the implanted power source supplies electrical power to the transmitter 32 and internal antenna 34 and data stored on the information storage component is transmitted from the implant component. The external antenna 44 receives the transmitted wave and this wave is interpreted in the external computer 46 to provide the stored data in a form that can be read by the appropriate personnel.

Figure 6:
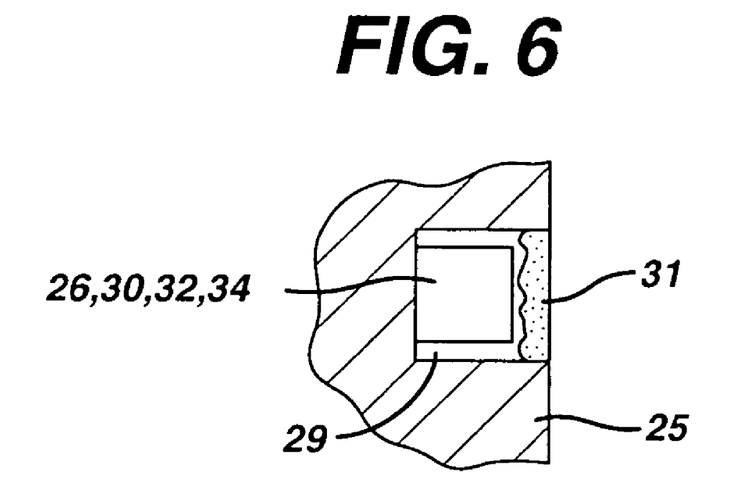
FIG. 6 is a partial cross-section of a portion of an orthopaedic element with an information storage portion, internal transmitter portion, internal antenna portion, and internal power source portion secured within a recess or cavity in the body portion of the orthopaedic element.
Figure 7:
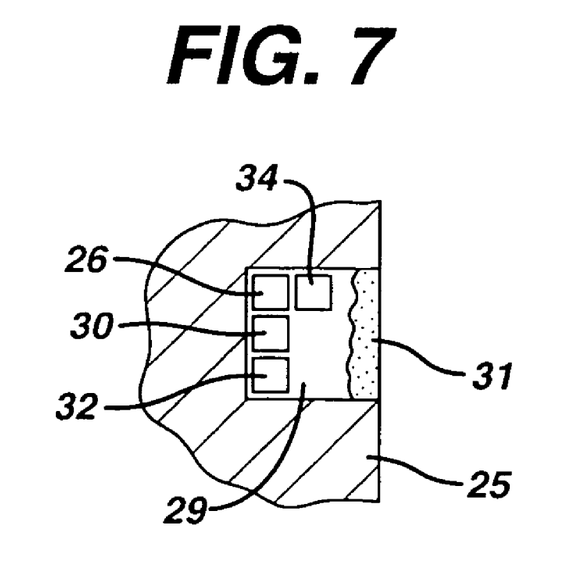
FIG. 7 is another partial cross-section of a portion of an orthopaedic element with an information storage portion, internal transmitter portion, internal antenna portion, and internal power source portion secured within a recess or cavity in the body portion of the orthopaedic element.

The information storage portion 26, transmitter portion 32, internal antenna portion 34 and internal power source portion 30 can be held in recesses or cavities in the bodies of the associated prosthetic components 13, 16, 17, 18, 19, 21, 23, 24 and 27 In FIGS. 6-7, the body of an orthopaedic element is indicated at 25 and the recess or cavity is indicated at 29. The recesses or cavities 29 are formed in areas of the prosthetic components 13, 16, 17, 18, 19, 21, 23, 24 and 27 where the presence of the recesses does not adversely affect the mechanical or physical properties of the prosthetic components, and will not offset the strength of the prosthetic components. In the embodiments of FIGS. 6-7, the recesses or cavities 29 extend inward from a non-articulating surface of the body 25 of the orthopaedic element. The sizes of the electronic portions 26, 30, 32, 34 can be selected to minimize the amount of space required to be taken up by these portions and to thereby minimize the size of the recess or cavity 29. The information storage portion 26, transmitter portion 32, antenna 34 and internal power source portion 30 are received in the recess 29 or on the surface of the body 25 of the orthopaedic element, and can be secured in position by various means. For example, the recess or cavity 29 could be covered with a piece of metal that is then welded to the surrounding part of the body 25 of the orthopaedic element. Alternatively, a liquid sealant, such as a biocompatible epoxy or polyurethane or silicone could be poured over the recess or cavity and allowed to cure to thereby permanently secure the information storage portion, transmitter portion and internal power portion to the body of the orthopaedic element. Cured sealant is indicated at 31 in FIGS. 6-7. The information storage portion 26, internal power source portion 30, internal transmitter portion 32 and internal antenna portion 34 can also be affixed in these recesses or cavities with a suitable adhesive if desired. The illustrated systems are assembled prior to implantation of the illustrated endoprosthesis systems.

And as described above, the information storage portion 26 and associated elements 30, 32, 34 (if used) could also be affixed to the exterior surface of a portion of the orthopaedic element or could be carried by a carrier (such as carrier 41 or 43) that is either permanently connected to the orthopaedic element or that is detachable from the orthopaedic element. It should be understood that it is anticipated that each of these ways of associating the information storage portion and its associated elements is expected to be useful for all of the orthopaedic elements described above.

It should be understood that the information storage portion 26, transmitter portion 32, internal antenna portion 34 and internal power source portion can be separate or discrete elements electrically connected. Alternatively two or more of these portions could be included as parts of a single electronic component that performs all of these functions. Accordingly, reference to an "information storage portion", a "transmitter portion" and an "internal power source portion" of an orthopaedic element is intended to encompass: a combination of an orthopaedic element and a single component with all of these functions and a combination of an orthopaedic element with two or more components performing one or more of these functions. Thus, although FIGS. 1, 2 and 3 each show different boxes for the portions 26, 28, 30, it should be understood that one, two or more components could be used in each of these embodiments. All of these components may be electronic.

Variations in the illustrated embodiments are possible. For example, an endoprosthesis or other orthopaedic element can be provided in the form of a kit with one or more of the information storage portion 26, power component portion 30, transmitter portion 32 and internal antenna portion 34 provided as a discrete element or as a single electronic component including circuitry that performs all of these functions. For example, the information storage portion 26, power supply portion 30, transmitter portion 32 and antenna portion 34 could be supplied as one or more separate discrete packages to be affixed to the patient's bones or implanted under the patient's skin instead of being associated with the orthopaedic element itself.

The orthopaedic elements of the present invention could be combined with other electronic features. For example, a joint endoprosthesis with information storage elements can be combined with joint space measurement devices such as those described in U.S. Provisional Patent Application Ser. No. 60/486,615 entitled "In Vivo Joint Space Measurement Device and Method," filed on Jul. 11, 2003 by Mark R. DiSilvestro, and the corresponding utility patent application (US 2005-0010301 A1) filed concurrently herewith by Mark R. DiSilvestro, Terry L. Dietz and Jason T. Sherman, the complete disclosures of which are incorporated by reference herein. A joint endoprosthesis system with information storage elements could also be combined with implant cycle counters such as those described in U.S. Provisional Application Ser. No. 60/486,762, entitled "In Vivo Joint Implant Cycle Counter", filed on Jul. 11, 2003 by Mark R. DiSilvestro, and the corresponding utility patent application (US 2005-0010299 A1) filed concurrently herewith by Mark R. DiSilvestro, the complete disclosures of which are incorporated by reference herein.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. An orthopaedic assembly comprising:
an orthopaedic element and a carrier element mechanically connected to the orthopaedic element,
the orthopaedic element having two ends, a body extending between the two ends, a length and an axis, the orthopaedic element comprising at least one of the following:
an orthopaedic prosthetic component;
an orthopaedic trauma product;
an orthopaedic instrument; and
an orthopaedic trial;
the carrier element having a male portion and an integral body, the body including an information storage portion, the information storage portion comprising a radio-frequency identification tag;
the carrier element being free from any drive mechanism;
wherein one of the ends of the orthopaedic element has an opening that receives the male portion of the carrier element to connect the carrier element to the orthopaedic element;
wherein the opening in the orthopaedic element and the male portion of the carrier element are sized and shaped to temporarily fix the position of the male portion of the carrier element relative to the orthopaedic element;
wherein at least a portion of the body of the carrier element is spaced axially from the body of the orthopaedic element; and
wherein the length of the body of the carrier element is less than the length of the body of the orthopaedic element.

2. The orthopaedic assembly of claim 1 wherein the carrier element is detachable from the remainder of the body.

3. The orthopaedic assembly of claim 1 wherein the carrier element is connected to the orthopaedic element through a threaded connection.

4. The orthopaedic assembly of claim 1 wherein the male portion and body of the carrier element are integral.

5. An orthopaedic assembly comprising a bone screw and a detachable carrier element, the bone screw having a threaded body and a head with an opening sized and shaped to be capable of receiving a portion of a surgical instrument for driving the screw into the patient's bone, the detachable carrier element including a body portion and an integral male portion received within the opening at the end of the bone screw to mechanically connect the detachable carrier element to the bone screw, the integral male portion of the carrier element and the opening at the end of the bone screw being sized and shaped so that the position of the carrier element relative to the bone screw is temporarily fixed, the body portion of the detachable carrier element including an information storage portion, the information storage portion comprising a radio-frequency identification tag, the detachable carrier element being free from any drive mechanism.

* * * * *